(12) United States Patent
Spitz et al.

(10) Patent No.: US 7,981,021 B2
(45) Date of Patent: Jul. 19, 2011

(54) CORRECTION OF STRESS URINARY INCONTINENCE

(75) Inventors: Robert M. Spitz, Waterford, CT (US); J. Anthony von Fraunhofer, Parkton, MD (US)

(73) Assignee: Contine Corporation, New London, CT (US)

( * ) Notice: Subject to any disclaimer, the term of this patent is extended or adjusted under 35 U.S.C. 154(b) by 0 days.

(21) Appl. No.: 12/790,468

(22) Filed: May 28, 2010

(65) Prior Publication Data

US 2010/0305395 A1  Dec. 2, 2010

Related U.S. Application Data

(60) Provisional application No. 61/217,199, filed on May 28, 2009.

(51) Int. Cl.
*A61F 2/02* (2006.01)
(52) U.S. Cl. .............................. 600/29; 600/37; 128/834
(58) Field of Classification Search .............. 600/29–32; 128/834, DIG. 25
See application file for complete search history.

(56) References Cited

U.S. PATENT DOCUMENTS

| | | |
|---|---|---|
| 1,949,863 A | 3/1934 | Hay |
| 2,141,040 A | 12/1938 | Holt |
| 2,146,574 A | 2/1939 | Hay |
| 2,638,093 A | 5/1953 | Kulick |
| 2,649,086 A | 8/1953 | Sluijter |
| 3,646,929 A | 3/1972 | Bonnar |
| 3,705,575 A | 12/1972 | Edwards |
| 4,019,498 A | 4/1977 | Hawtrey et al. |
| 4,031,886 A | 6/1977 | Morhenn |
| 4,139,006 A | 2/1979 | Corey |
| 4,823,814 A | 4/1989 | Drogendijk et al. |
| 4,857,041 A | 8/1989 | Annis et al. |
| 4,875,898 A | 10/1989 | Eakin |
| 4,920,986 A | 5/1990 | Biswas |
| 5,007,894 A | 4/1991 | Enhorning |
| 5,036,867 A | 8/1991 | Biswas |
| 5,041,077 A | 8/1991 | Kulick |
| 5,299,581 A | 4/1994 | Donnell et al. |
| 5,386,836 A * | 2/1995 | Biswas ........................ 128/885 |
| 5,618,256 A | 4/1997 | Reimer |
| 5,771,899 A | 6/1998 | Martelly et al. |

(Continued)

FOREIGN PATENT DOCUMENTS

GB  670349 A  4/1952

OTHER PUBLICATIONS

International Search Report and Written Opinion for PCT/US2010/036689 dated Feb. 17, 2011.

*Primary Examiner* — Charles A Marmor, II
*Assistant Examiner* — Carrie Dorna
(74) *Attorney, Agent, or Firm* — Scott E. Kamholz; Foley Hoag LLP

(57) ABSTRACT

Devices for treating stress incontinence, having a horizontal proximal portion supported on the pubococcygeus muscle and a distal portion extending downward and away from the proximal portion at an angle approximating the vagina in an erect female as it passes down and between the anterior segments of the pubococcygeus. The distal portion may terminate with a protrusion that is positioned to provide midurethral support, thereby preserving the urethovesical angle.

24 Claims, 11 Drawing Sheets

U.S. PATENT DOCUMENTS

| | | |
|---|---|---|
| 5,894,842 A | 4/1999 | Rabin et al. |
| 6,142,928 A | 11/2000 | Zunker et al. |
| 6,216,698 B1 | 4/2001 | Regula |
| 6,311,389 B1 | 11/2001 | Uosaki et al. |
| 6,418,930 B1 | 7/2002 | Fowler |
| 6,460,542 B1 | 10/2002 | James |
| 6,808,485 B2 | 10/2004 | Zunker |
| 7,223,228 B2 | 5/2007 | Timm et al. |
| 7,351,195 B2 | 4/2008 | Farrell |
| 7,387,603 B2 | 6/2008 | Gross et al. |
| 7,628,155 B2 | 12/2009 | Carey |
| 7,673,631 B2 | 3/2010 | Astani et al. |
| 7,771,344 B2 | 8/2010 | Ziv |
| 2004/0034275 A1 | 2/2004 | Forsell |
| 2004/0084054 A1 | 5/2004 | Kaseki et al. |
| 2004/0158122 A1 | 8/2004 | Guerquin |
| 2005/0016545 A1 | 1/2005 | Nissenkorn |
| 2007/0244352 A1 | 10/2007 | Ziv |
| 2008/0009662 A1 | 1/2008 | Bartning et al. |
| 2008/0009663 A1 | 1/2008 | Bartning et al. |
| 2008/0033230 A1 | 2/2008 | Bartning et al. |
| 2008/0149109 A1 | 6/2008 | Ziv |
| 2008/0228027 A1 | 9/2008 | Guerquin et al. |
| 2008/0281149 A1 | 11/2008 | Sinai et al. |
| 2009/0203959 A1 | 8/2009 | Ziv et al. |
| 2009/0266367 A1 | 10/2009 | Ziv et al. |
| 2009/0318750 A1 | 12/2009 | Ziv et al. |
| 2010/0217068 A1 | 8/2010 | Ziv et al. |

* cited by examiner

CORRECTION OF STRESS URINARY INCONTINENCE

CROSS-REFERENCE TO RELATED APPLICATION

This application claims the benefit of U.S. provisional application Ser. No. 61/217,199, filed May 28, 2009, which is hereby incorporated herein by reference.

BACKGROUND

Although stress urinary incontinence is a frequent problem in women, there are few treatment strategies short of surgery and little attention paid to the early years during which a woman experiences the problem. In *The Surgeon: Journal of the Royal Colleges of Surgeons of Edinburgh and Ireland*, 2008 December; 6(6):366-72, Long et al state, "Urinary incontinence is a social burden for up to one-third of the adult female population." In 1995, Sandvik, with the Norwegian Department of Public Health and Primary Health Care, reviewed 13 studies with the conclusion that there was an incontinence prevalence of 20-30% in young women and 30-40% in middle aged women, with almost half having predominantly stress incontinence and one third having mixed incontinence. A study by Nygaard, Thompson, Svengalis, and Albright (1994) showed that 28% of 156 nulliparous college varsity athletes with a mean age of 19.9 years experienced urine loss during sports. Seventeen percent of the female athletes reported that their problem began in junior high, and 40% reported that the problem began in high school. A retrospective study of 104 female Olympians (16.7% nulliparous) (Nygaard, 1997) reported 35.8% of the athletes experienced UI during sports.

Vaginal pessaries have been used for decades, but they have been generally more successful in the treatment of pelvic organ prolapse than urinary incontinence. These pessaries do not account for the angulation between the upper and lower vagina that occurs when a woman is in an upright position, and drawings depicting their proper placement in vagina virtually all depict them placed into a straight vagina. Effectiveness of pessaries depends upon their ability to provide appropriate support when the woman is in an upright position as this is the position in which incontinence generally occurs. Because of their shape and rigidity, when placed in the vagina existing pessaries force the vagina into a straight configuration and either support the bladder more than the urethra, or they support both the urethra and the bladder eliminating the posterior urethrovesical angle (FIG. 10).

U.S. Pat. No. 4,823,814 by Drogendijk et al. discloses a pessary for treatment of both prolapse of internal female sex organs and urinary incontinence. The pessary is oval-shaped and bowed along a major axis of the oval. An elastic strip along an edge of the pessary may be expanded to close off the urethra and inhibit urine flow.

Pelvic floor strengthening exercises are an occasional topic of discussion between doctor and patient, but are rarely employed in a systematic way. Until the problem becomes particularly bothersome, women typically deal with the problem by using absorbent pads and curtailing activities that are likely to cause incontinence. Vaginal pessaries have been more helpful for pelvic organ prolapse than for incontinence, are used primarily in the elderly, and have the disadvantage of only being available when prescribed by a qualified health practitioner. Many active women would prefer to handle the problem themselves, much as they do with tampons for the inconvenience of menses, until the problem is severe enough to consider surgery. To have a disposable product that they could use as desired would be attractive and would allow many women to continue physical activities that they currently avoid.

U.S. Pat. No. 6,808,485 discloses a helical device formed of a compressible, resilient, biocompatible material to relive urinary incontinence. The device is insertable and removable by the user. U.S. Pat. Nos. 4,823,814 and 6,808,485 are incorporated herein by reference in their entireties.

SUMMARY

Disclosed herein are devices for correcting stress urinary incontinence. The devices may include a horizontal proximal portion supported on the pubococcygeus muscle and a distal portion extending downward and away from the proximal portion at an angle approximating the vagina in an erect female as it passes down and between the anterior segments of the pubococcygeus. The distal portion may terminate with a protrusion that is positioned to provide midurethral support, thereby preserving the urethovesical angle.

The device conforms to the shape of the vagina and the protrusion (or "knob") is positioned posterior to the mid-urethra and applies sufficient pressure to limit urethral hypermobility, thus preventing stress urinary incontinence, while avoiding obstruction during intentional voiding. Additionally, supporting only the mid-urethra and not the upper urethra and bladder allow structures superior to the knob to descend creating a kink in the urethra to prevent further unintentional discharge of urine. The angled skeleton of the frame of this device ensures that downward pressures of the abdominal cavity will help to hold the horizontal upper portion of the device against the posterior pelvic floor muscles reducing the likelihood of expulsion.

DETAILED DESCRIPTION

Figure 1:
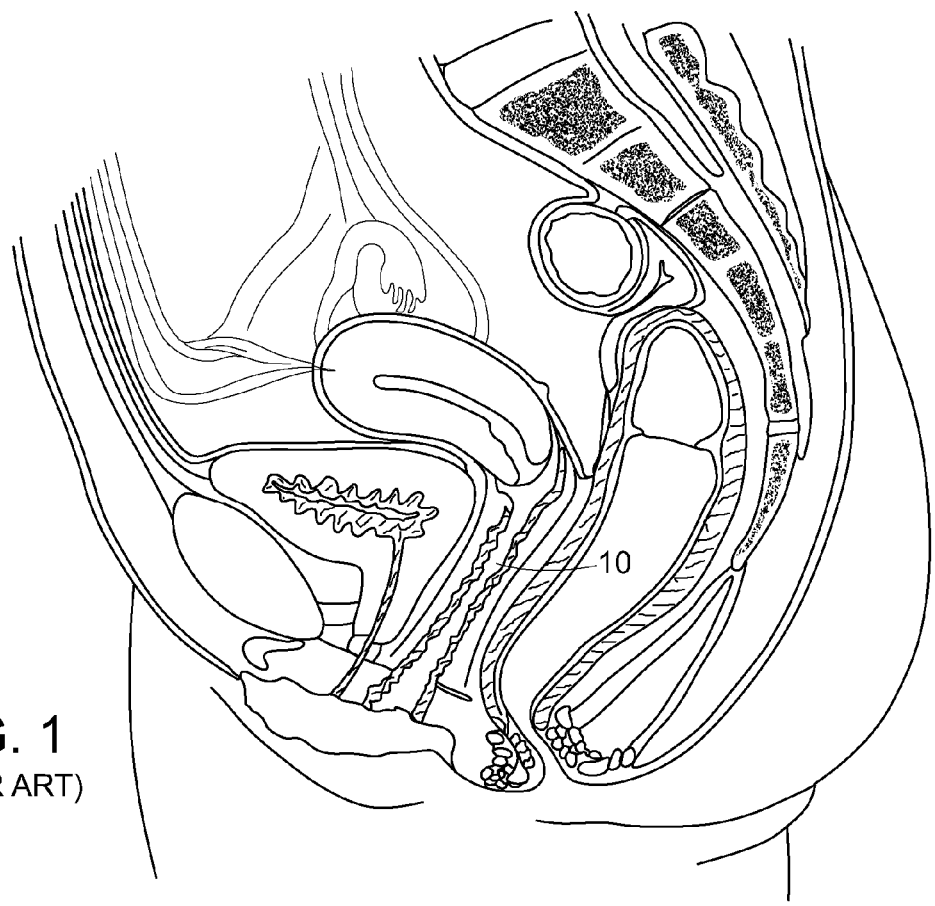
FIG. 1 is an anatomical drawing of a female pelvis from the prior art.
Figure 10:
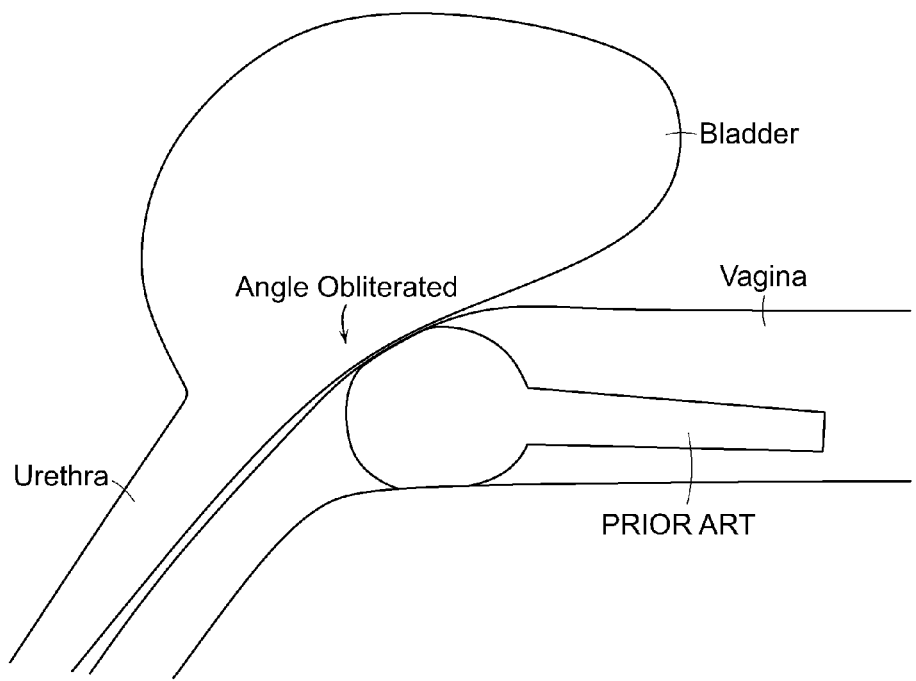
FIG. 10 schematically shows how a prior-art pessary obliterates the urethrovesical angle.

As illustrated in FIG. 1, most prior art anatomic drawings of the female pelvis have shown the vagina 10 to be straight, or nearly straight, when viewed in the sagittal plane. These drawings are based on cadaver dissections and do not reflect the true anatomy of the normal erect live adult female. Ring-shaped vaginal pessaries 12, illustrated in FIG. 2, having an incontinence knob 14 have been used for decades, but they have been generally more successful in the treatment of pelvic organ prolapse than urinary incontinence. These ring-shaped vaginal pessaries 12 do not account for the angulation between the upper vagina 16 and lower vagina 18, and drawings depicting their proper placement in vagina 10 virtually all depict them placed into a straight vagina. Because of their shape and rigidity, when placed in the vagina 10 they force the vagina into a straight configuration and either support the bladder 20 more than the urethra 22, or they support both the urethra and the bladder eliminating the posterior urethrovesical angle (FIG. 10).

Figure 3:
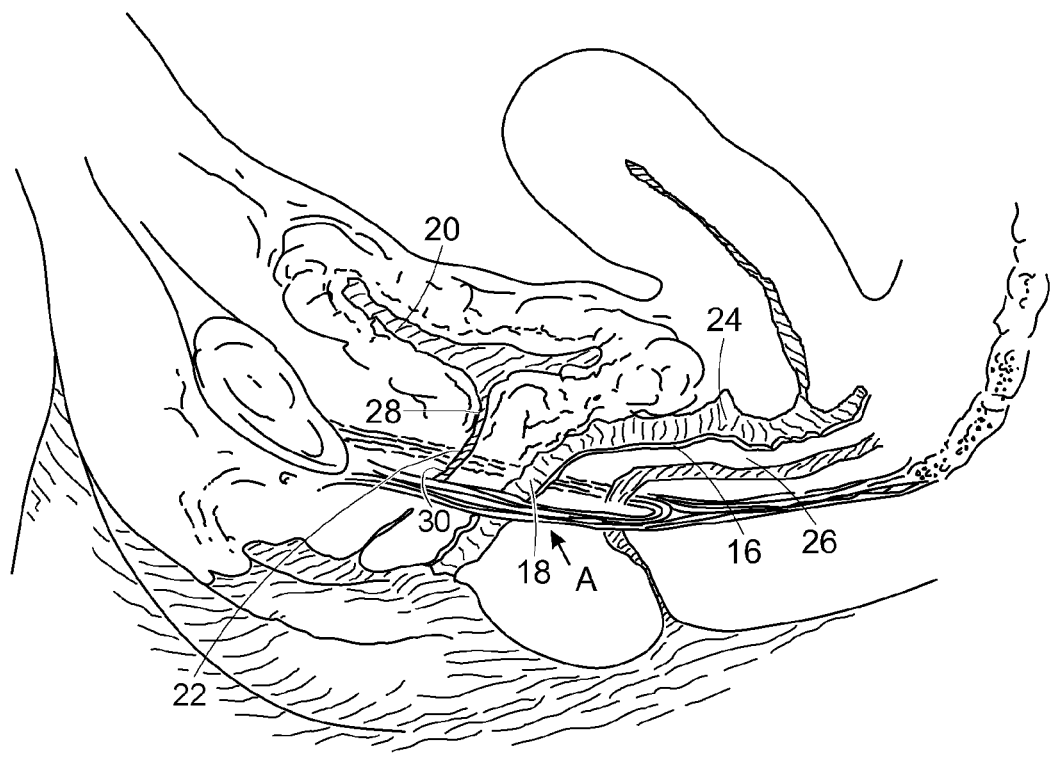
FIG. 3 is a more accurate anatomical drawing of an erect, live female pelvis.

In recent years, there have been changes in the understanding of female pelvic anatomy and mechanisms of continence. Most anatomic drawings of the female pelvis have shown the vagina to be straight, or nearly straight, when viewed in the sagittal plane. These drawings are based on cadaver dissections and do not reflect the true anatomy of the normal erect live adult female. A more accurate depiction of female pelvic anatomy is seen in FIG. 3, (taken from FIG. 1.17 Nichols D & Randall C. (1989) *Vaginal Surgery*. (p. 23) Baltimore, Md. Williams & Wilkins) which shows approximately a 135° angle between the lower vagina 18 (posterior to the urethra 22) and the upper vagina 16, so that the upper vagina lies in an almost horizontal plane where it is supported by the levator muscles 24 of the pelvic floor 26. This anatomy is confirmed by MRI imaging of healthy adult women (Fielding J R, et al., "MR Imaging of the Female Pelvic Floor in the Supine and Upright Positions." JMRI 1996(6):961-3; Harvey M & Versi E. 2003. "MRI Studies in the Evaluation of Pelvic Floor Disorders." In Drutz H P, Herschon S & Diamant N E (Eds.), *Female Pelvic Medicine and Reconstructive Pelvic Surgery* (pp. 145-157) London: Springer). The initial portion of the vagina rises at about a 45° angle passing between the pubococcygeus muscles. These muscles come together and fuse in the midline behind the rectum. The upper vagina lies in a horizontal position supported by the fused muscles with the rectum passing between the front surface of the muscle and the back surface of the vagina.

Most pessaries are relatively flat and round and when they are positioned properly in the vagina the lateral portion of the pessary is supported by the separated anterior segments of the pubococcygeus muscles while the upper end of the pessary lies on the fused segment just like the upper vagina. If the cervix is present, the upper portion of the pessary will typically rest in the posterior formix of the vagina just behind the cervix. From this position a pessary is able to support the bladder and the uterus, but not the urethra. This contributes to the frequent failure of conventional pessaries to prevent urinary incontinence as will be explained further below.

Urinary continence is maintained by urethral pressure exceeding intravesical (bladder) pressure at rest and during physical activities. The "Hammock Hypothesis" of urinary continence (Delancey J O, "Structural support of the urethra as it relates to stress urinary incontinence: the hammock hypothesis." *Am J Obstet Gynecol*. 1994 June; 170(6):1713-20) states that increases in urethral closure pressure during a cough arise because the urethra is compressed against the firm backstop of a hammock-like supportive layer under the urethra and vesical neck. Damage to tissues that comprise the "hammock" allows for excess movement of the urethra in response to any physical force from above, such as sneezing, coughing, laughing and physical activity. This urethral hypermobility allows pressure inside the bladder to momentarily exceed urethral pressure resulting in involuntary loss of urine.

Another factor relating to continence is the posterior urethrovesical angle that is formed where the urethra enters the bladder. The normal angle is clearly seen in FIG. 3. The urethra 22 enters the body in the same direction as the lower vagina 18 and as the vagina falls back into its horizontal position, the posterior aspect of the bladder 20 lies above it, forming the posterior urethrovesical angle.

Figure 2:
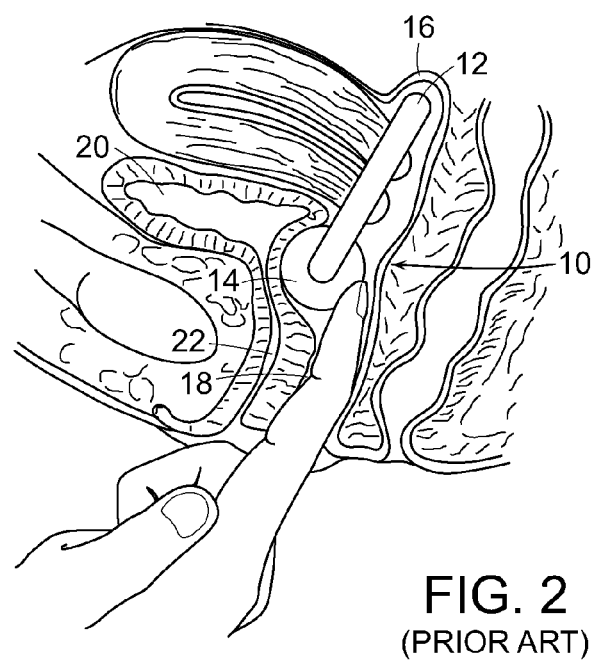
FIGS. 2, 2A, and 2B illustrate prior art pessary rings as inserted for controlling urinary incontinence.
Figure 2A:
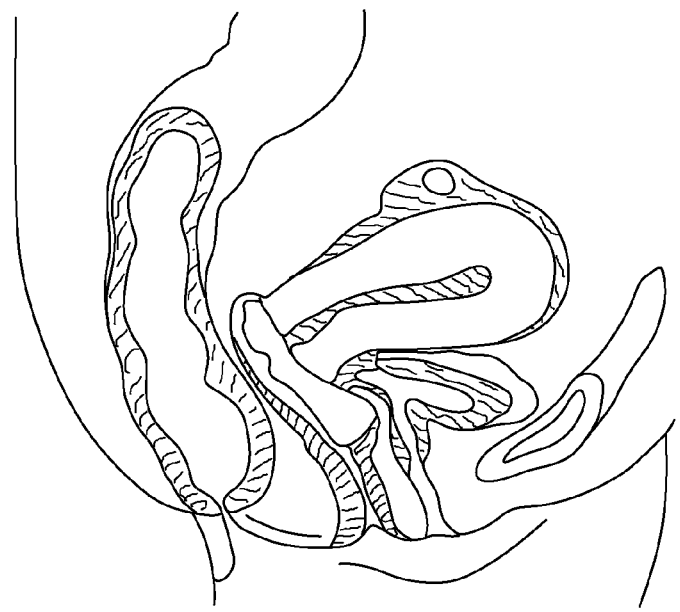
Figure 2B:
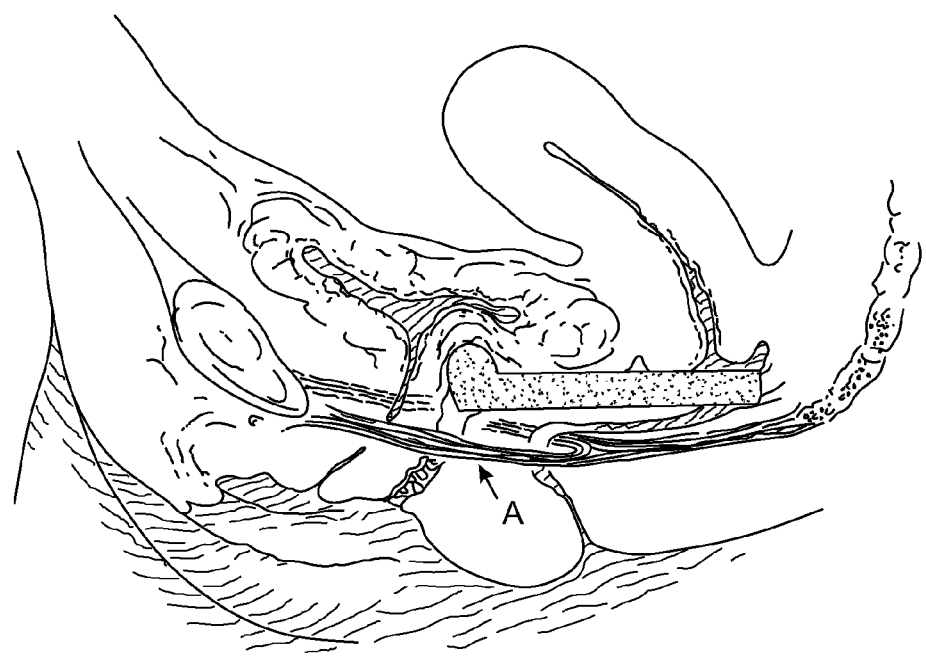

Currently available support devices (i.e. pessaries) were designed based on the assumption that the vagina is straight; consequently they do not account for the correct anatomy in the erect position. As most incontinence occurs when the woman is erect, this is a serious deficiency that contributes to the frequent failure of these devices to adequately correct urinary incontinence. The pessaries that are intended for correction of incontinence generally have a knob that is intended to compress the urethra or bladder neck. This is demonstrated in FIGS. 2, 2A, and 2B, showing the position of the prior-art pessaries. Close examination reveals that the vagina is depicted as straight in each illustration. However, because the pessary lies on the horizontal pubococcygeus muscles, the support knob will often lie against the posterior aspect of the bladder rather than at its intended position supporting the urethra or bladder neck. In cases where a pessary is successful in correcting urinary incontinence, it has been shown that the pessary increases urethral closure pressure and diminishes mobility of the urethra, both effects that are consistent with the hammock hypothesis of urinary continence. In these situations, the knob of the pessary is undoubtedly initially positioned at the bladder neck, but this may not remain the case, and there are several factors that contribute to these pessaries not remaining in place. The upper edge of a pessary will usually slip up behind the cervix and remain in this position. If the pessary is not of sufficient length, the knob will not reach the bladder neck and will lie under the trigone of the bladder just above the urethrovesical junction (FIG. 10). In this position it can eliminate the posterior urethrovesical angle compounding the problem of incontinence. Because pessaries are typically round, the length of the pessary is limited by the width that the vagina will accommodate in any individual woman. This prevents the knob from being properly positioned. Also, because the pessaries lie in a single plane and are essentially two-dimensional, they can easily rotate so that the support knob lies off-center, unable to support the bladder neck even if there is sufficient length to reach it. This sometimes occurs as stool passes through the rectum immediately posterior to the pessary, particularly in the constipated woman (the rectum and vagina are in closest proximity above the pubococcygeus muscles).

Figure 11:
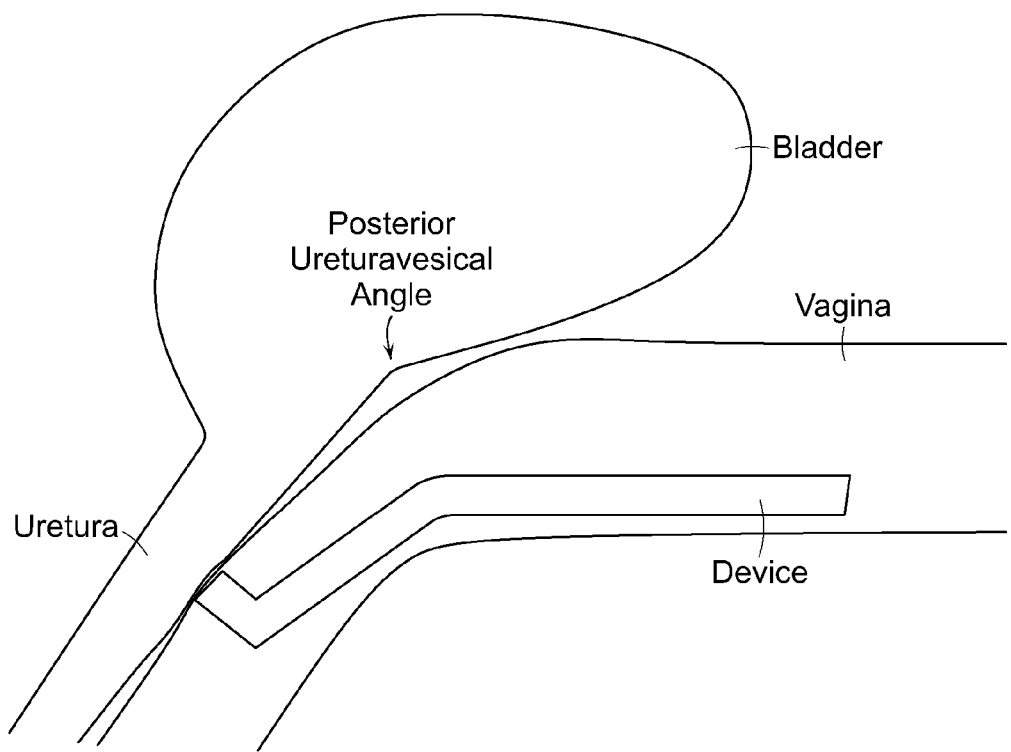
FIG. 11 schematically shows how the present device preserves the urethrovesical angle and directs urethral support to a midurethral position.

A device as described herein differs from conventional pessaries in several significant ways. A proximal portion of the device, like conventional pessaries, rests on the pubococcygeus muscles for its support. There is, however, a distal portion that extends away and downward from the proximal portion at approximately 45° below horizontal (i.e., at about a 135-degree angle from the horizontal portion) on which is located a protrusion that provides urethral support. (The terms "proximal" and "distal" were assigned based on the positions of the device relative to the body of the user. Hence, the "proximal" portion of the device is closer to the core of the user's body, while the "distal" portion is further outward.) The angle may be in the range of about 100 degrees to about 160 degrees, about 100 degrees to about 150 degrees, about 105 degrees to about 150 degrees, about 120 degrees to about 145 degrees, 115 degrees to about 145 degrees, about 125 degrees to about 145 degrees, about 130 degrees to about 140 degrees, about 135 degrees, and/or exactly 135 degrees. This extension follows the natural orientation of the vagina positioning support under the midurethra rather than at the bladder neck or higher. Moving support from the posterior aspect of the bladder, or bladder neck, to the midurethra mimics advances in sling surgeries that were previously placed in support of the bladder neck and that are now usually placed at the level of the midurethra. It is consistent with the hammock hypothesis and avoids elimination of the posterior urethrovesical angle (FIG. 11).

In addition to moving the support element under the urethra, creating a more 3-dimensional device instead of a flat one provides a more natural fit between the device and the vagina, stabilizing the position of the device. The presence of an angle in the device matching the natural angle of the vagina inhibits the device from sliding towards the upper vagina moving the support knob out of position. Also, because the extension projects downward between the pubococcygeus muscles, the muscles prevent rotational displacement of the support knob. There is no need for the upper portion of the device to extend all the way to the top of the vagina, and this should avoid irritation or erosion of the vaginal mucosa in the posterior formix as is sometimes seen with conventional pessaries. In fact, there does not necessarily have to be a connection between the right and left side of the device near the top, and there may be advantages to not connecting them. One advantage is eliminating a spot where stool might dislodge the pessary from the desired position. A second advantage is that it might be easier to preload the device into a tampon-like inserter as independent arms could overlap one another within the inserter. With independent support arms, they could extend further anterior along the pubococcygeus muscles (i.e., distally extending in a horizontal plane). They would pass alongside the urethra on each side providing added stability to the device by utilizing the more stable portion of the pubococcygeus muscles near their insertion point on the posterior aspect of the pubic symphysis. Also, they would provide some additional stability to the upper urethra.

One additional fault of conventional pessaries is that they tend to be overly bulky, making them difficult to self insert. As they are designed to treat pelvic organ prolapse in addition to urinary incontinence, they are both bulky and stiff. Relatively little force is needed to prevent urethral hypermobility, so for a dedicated incontinence device proper position of support is more important than strength or rigidity. This allows the present device to be made of more slender parts, making it more appealing and less intimidating than current pessaries.

Stress urinary incontinence occurs primarily because of urethral hypermobility, however it has been shown that surgical support procedures that eliminate the posterior urethrovesical angle through excessive support of the bladder 20 can induce incontinence, even if it did not exist prior to surgery. A key to correction of stress incontinence is limiting urethral mobility without creating loss of the posterior urethrovesical angle. In fact, allowing the bladder 20 or upper urethra 28 to descend posteriorly while supporting the mid-urethra 30, thus creating a "kinking effect," may play a significant role in the success of mid-urethral sling surgeries that are performed for correction of stress incontinence.

Figure 4:
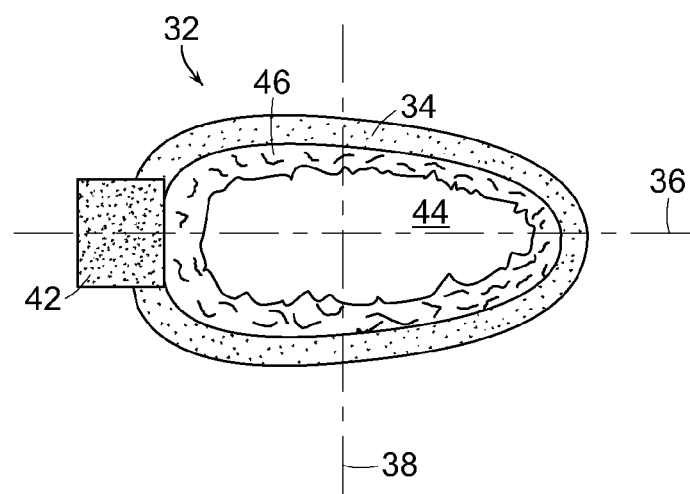
FIG. 4 is top planar view of a pessary ring for controlling urinary incontinence.
Figure 5:
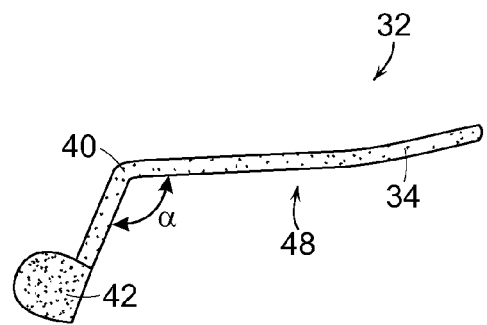
FIG. 5 is a side view of the pessary ring of FIG. 4.

One embodiment of a device 32, illustrated in top planar view in FIG. 4 and side view in FIG. 5, prevents female stress urinary incontinence by restricting urethral mobility without loss of the posterior urethrovesical angle. By conforming more precisely to the female pelvic anatomy and function the device 32 overcomes inadequacy of existing designs. The device 32 is suitable for direct to consumer marketing as a disposable device that is used much like a tampon.

Figure 6:
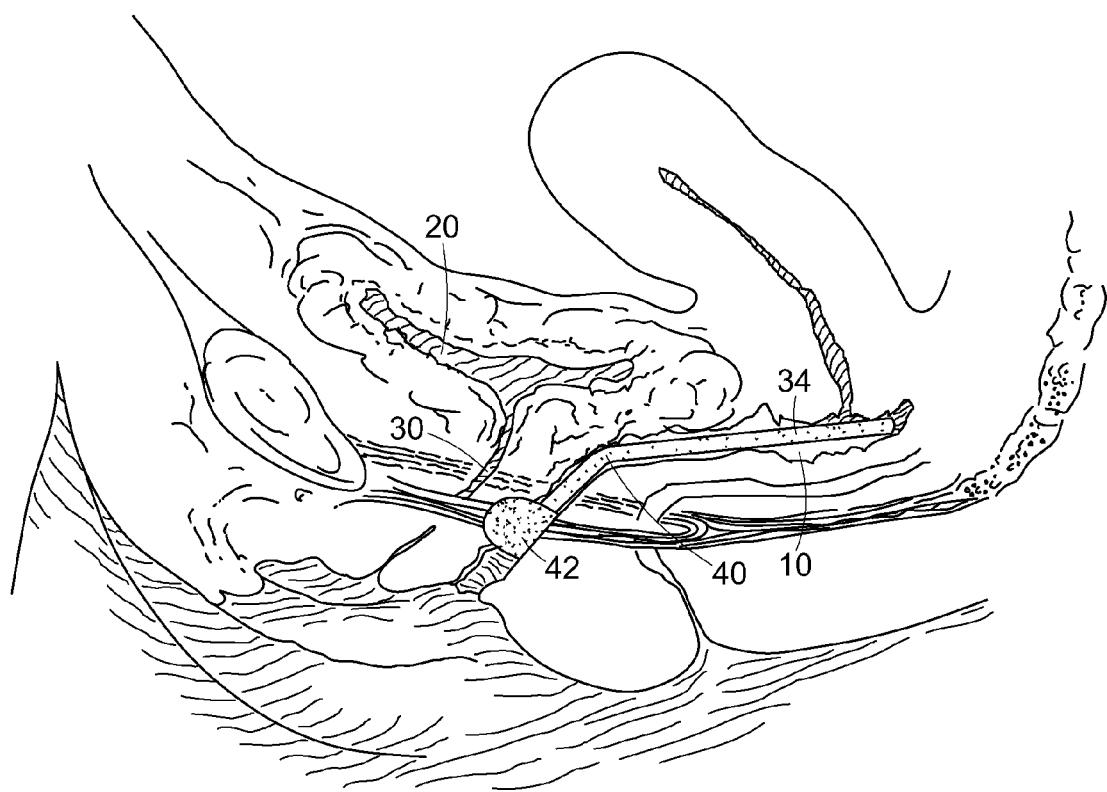
FIG. 6 illustrates the pessary ring of FIG. 4 as inserted for controlling urinary incontinence.

The illustrated device 32 has a skeleton 34 that is generally oval shaped having a major axis 36 and a minor axis 38 perpendicular to the major axis. Referring to FIG. 6, the skeleton 34 is angled at an inflection point 40 to conform to the shape of the normal vagina 10 when viewed laterally, and a knob 42 that is held in proper position posterior to the mid-urethra 30 by the skeletal frame 34 of the device. Some rigidity of the skeleton 34 is required. Rigidity is most important along the length of the device so that the knob 42 will not move upward towards the bladder 20.

Referring back to FIGS. 4 and 5, clinical testing may show benefit to some flexibility of the skeleton 34 so that while an inflection point 40 angle, α, of 118° is shown, in practice this angle may vary somewhat when the device 32 is in use. An angle of from 100° to 160° is believed acceptable. Additional possible angle ranges are given elsewhere. Flexibility across the width of the skeleton 32 may facilitate compression for ease of insertion and subsequent expansion for better retention within the vagina. The space 44 allowed in the central portion of the skeleton 32, together with the angulation of the skeleton, will allow the bladder to descend posteriorly maintaining the posterior urethrovesical angle and possibly allowing the above described kinking effect (FIG. 11). A portion of this space 44 may optionally be eliminated with the addition of an absorbent material 46 for use as a disposable combined incontinence device and absorbent tampon during menses.

Clinical trials will also determine whether it is preferable for the knob 42 to be rigid, such as the ones on currently marketed pessaries, or somewhat compressible for comfort and for ease of intentional voiding. Incontinence trials performed to date have shown some success using a PVA sponge material vaginally for support of the urethra, and a cotton/rayon combination such as found in tampon composition may be desirable.

Dynamic MRI imaging of the pelvis in healthy females in the erect position have shown that during valsalva there is contraction of the pelvic musculature that provides support to the urethra, contributing to continence. In many women with early stages of stress incontinence the primary defect is in the endopelvic fascial support of the urethra and the urethropubic suspensory tissue while the pelvic floor muscles remain intact. Contraction of the pelvic floor muscles, as occurs involuntarily during activity, will help move the knob 42 of the device 32 anteriorly and superiorly for better restriction of urethral mobility. This may allow a knob 42 made of a somewhat compressible material to be sufficient with the advantage of avoiding obstruction of the urethra while intentionally voiding. Also, the downward forces from the abdominal cavity towards the pelvis during activity and valsalva sometime cause expulsion of existing pessaries because their rigid shape straightens the vagina into a more vertical position than normal. The angled skeleton of this device ensures that those pressures will help to hold the horizontal upper portion 48 of the device against the posterior pelvic floor muscles reducing the likelihood of expulsion. The combination of the upward force of the pelvic floor anteriorly and the downward forces from the abdominal cavity posteriorly may also produce a lever effect resulting in greater support of the knob against the mid-urethra.

Figure 7:
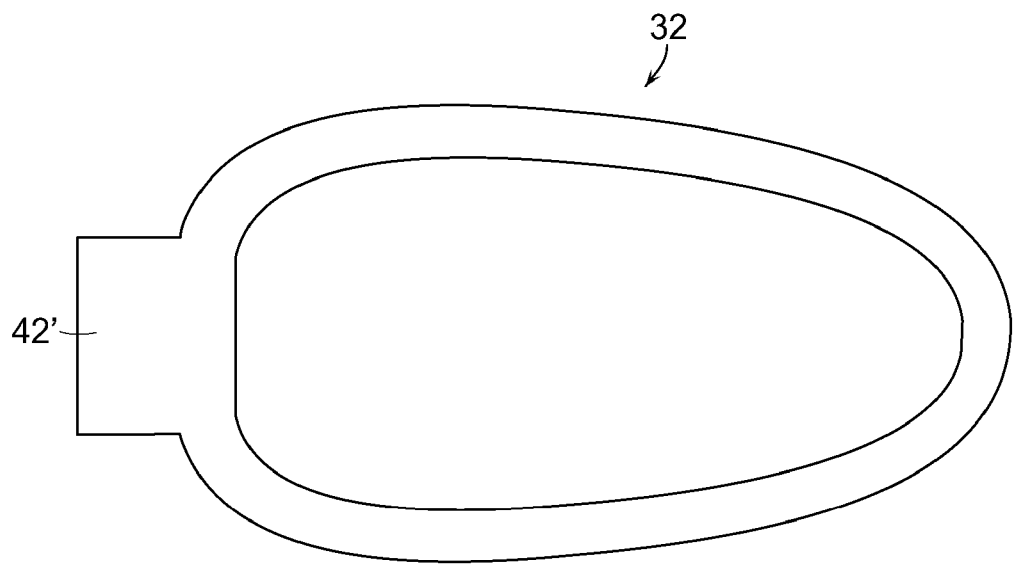
FIG. 7 is a top planar view of another embodiment of a pessary ring for controlling urinary incontinence.

Referring to FIG. 7, clinical trials might demonstrate that the compressible knob 42' on the device 32 might not have to be made of a different material, and that if the angle alone is sufficient to provide functionality then it might be possible to mold the device as a single piece. The previous embodiment (FIGS. 4 and 5) involving two materials comes from trialing a compressible material without the angled skeleton of the device. Although it worked well, the compressible material might ultimately prove unnecessary.

Figure 7A:
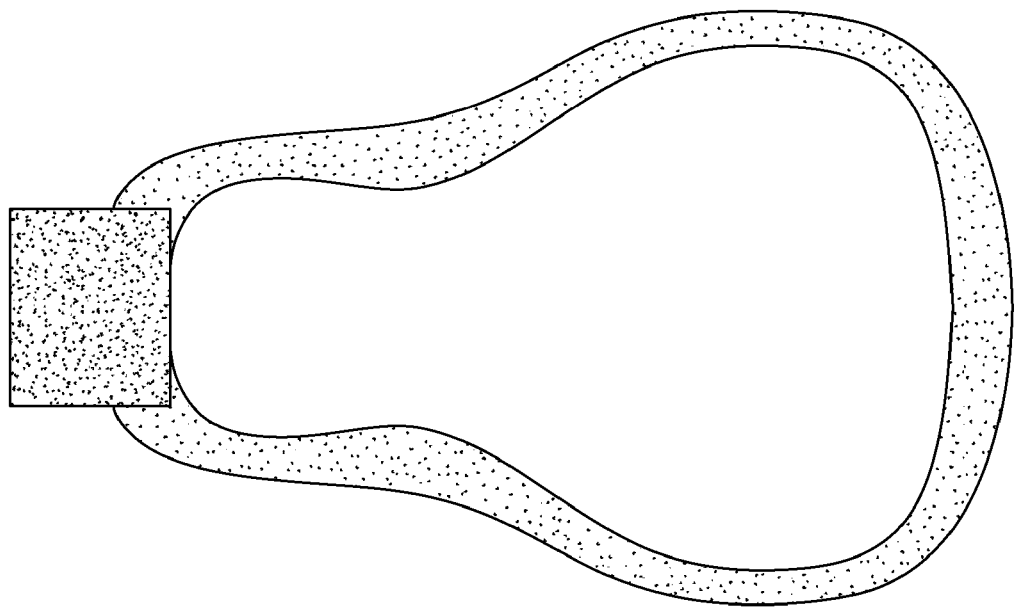
FIG. 7A shows an alternate embodiment.

FIG. 7A shows an alternative embodiment which progressively narrows from its proximal end to its distal end, with pronounced narrowing at the inflection. The ring is thickened at the inflection to provide greater rigidity there compared to the more proximal and distal regions.

Figure 8:
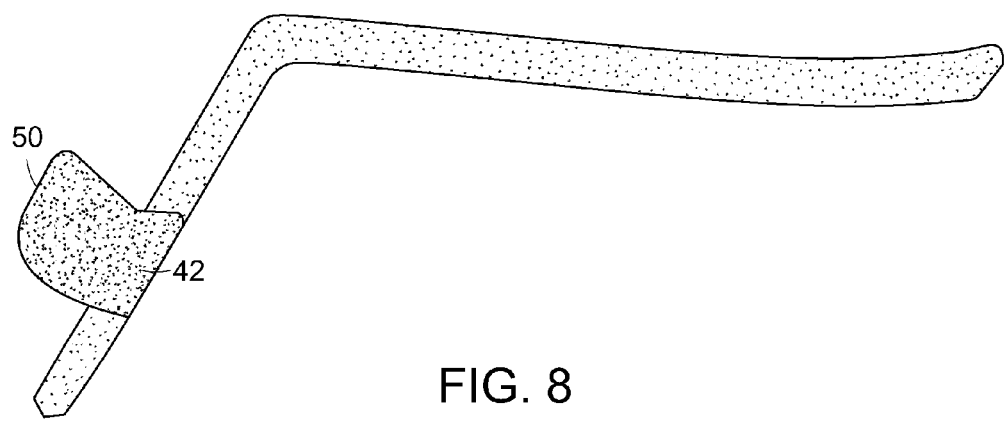
FIG. 8 is a side view of a pessary ring for controlling urinary incontinence illustrating an alternative shape for a knob.

Referring to FIG. 8, the knob 42 may have any shape effective to apply sufficient pressure to the mid-urethra to limit urethral hypermobility and allow the kinking effect to occur. Shaping the knob 42 so that contacting surface 50 is more angular and less rounded will achieve this objective.

Figure 9:
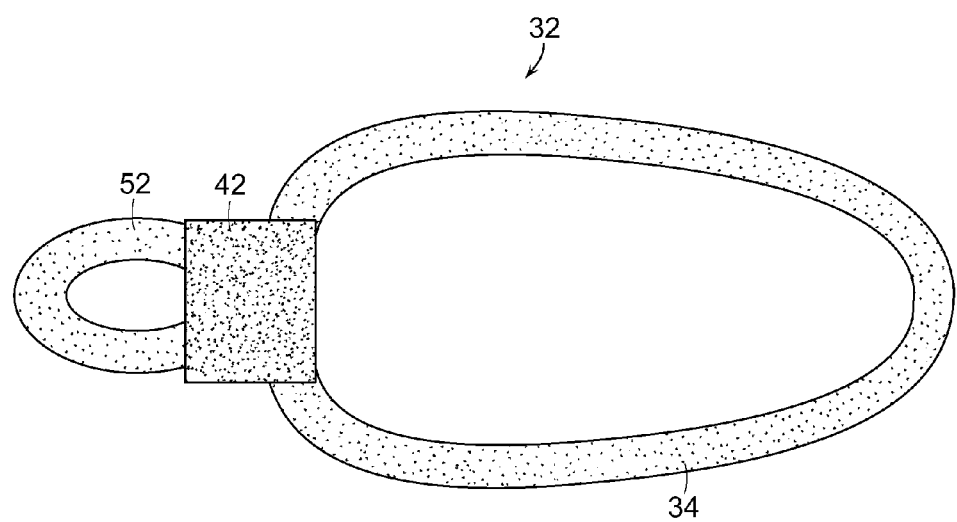
FIG. 9 is a top view of a pessary ring for controlling urinary incontinence illustrating inclusion of a loop to assist removal.
Figure 9A:
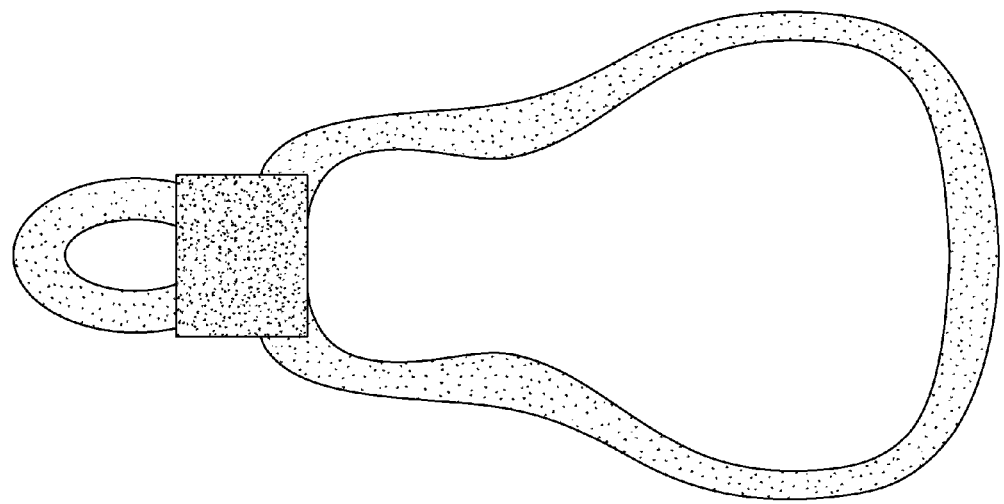
FIG. 9A shows an alternate embodiment.

Referring to FIG. 9, preferably there is an extraction aid 52 positioned adjacent the knob 42 to aid in removal of the device 32. The extraction aid may be as simple as a string such as found on tampons. Or, as illustrated, formed as an integral part of the skeleton 34. Extraction aid 52 may be a ring extending past the knob 42 and sized to be hooked by a finger for removal of the device 32. FIG. 9A shows an alternate embodiment similar to FIG. 7A. In other embodiments, an extraction aid may be attached to arms of the device; they may be positioned in such as way as to facilitate compression of the device for removal.

Figure 12:
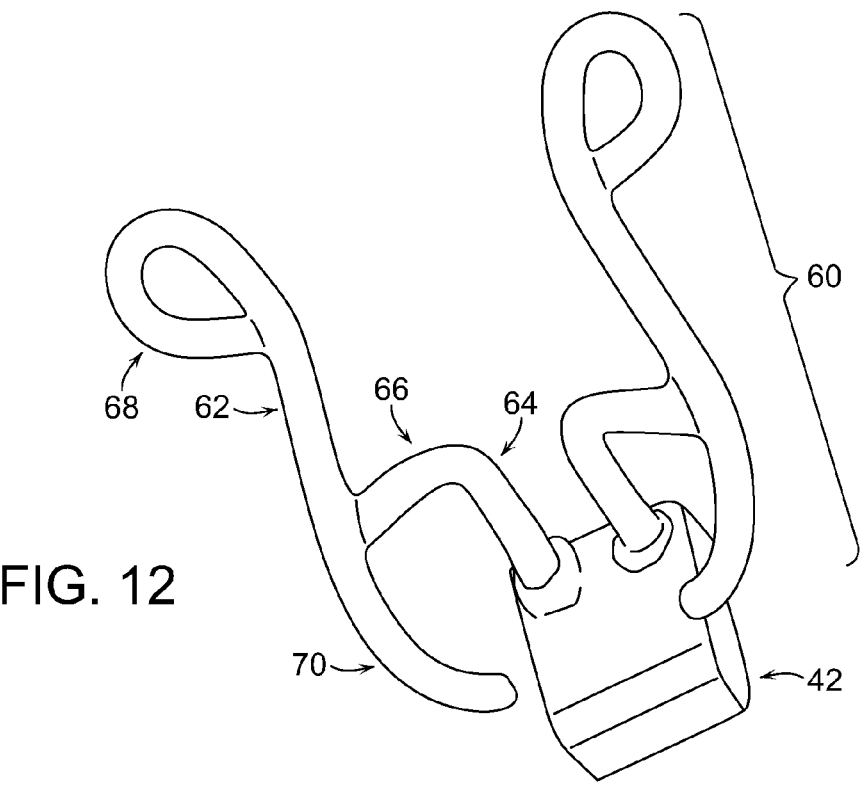
FIGS. 12-15 show an alternative embodiment of a stress urinary incontinence treatment device.
Figure 13:
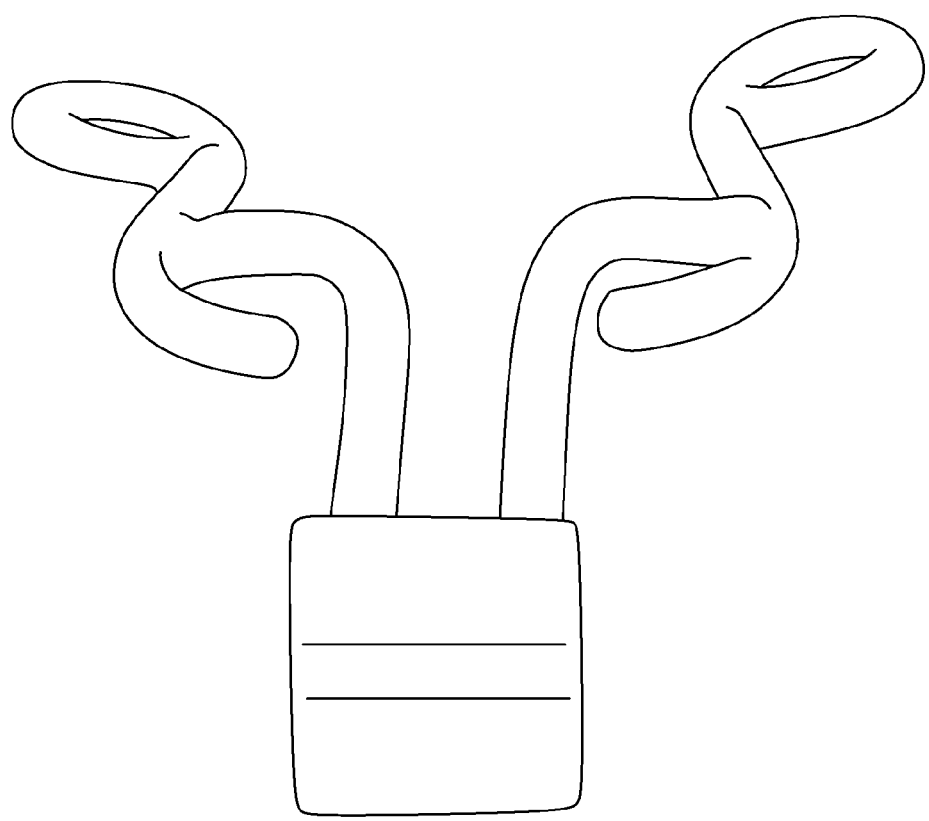
Figure 14:
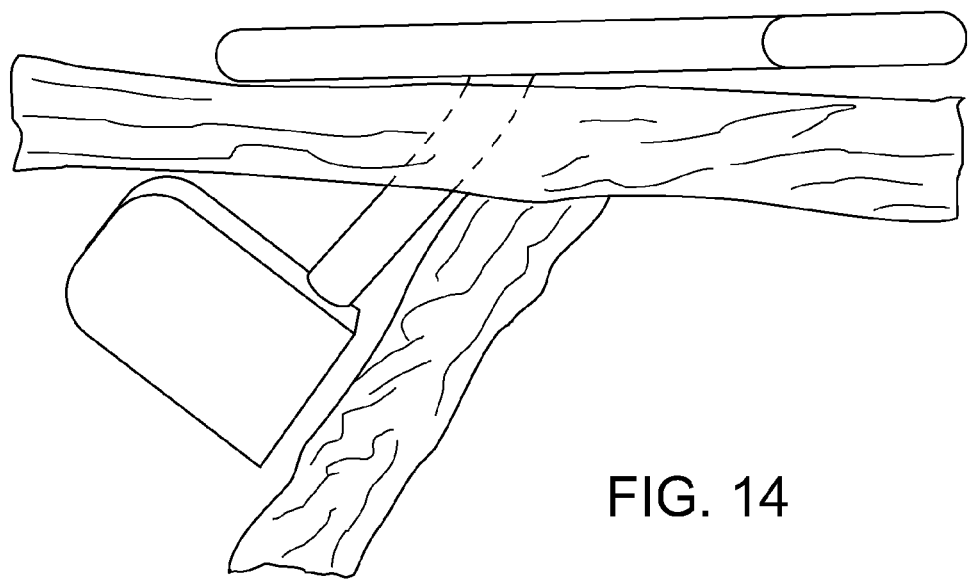
Figure 15:
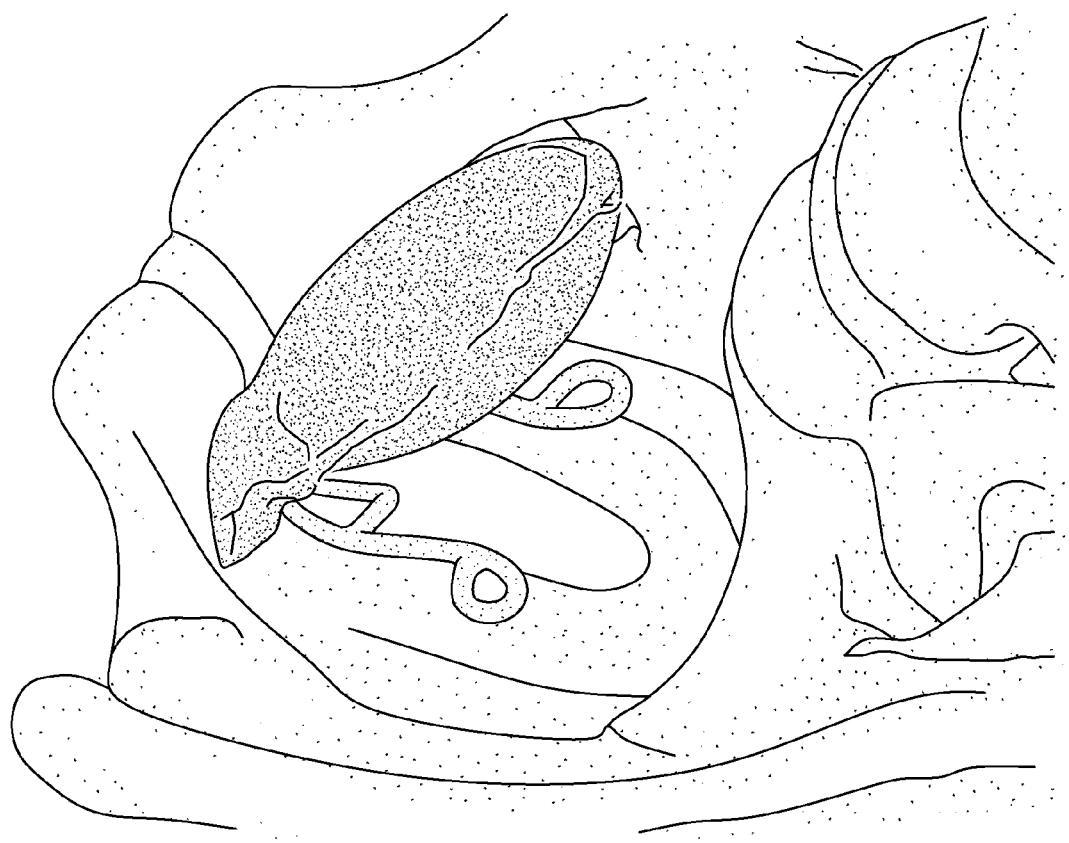

FIGS. 12-15 depict another exemplary embodiment of a stress urinary incontinence correction device. FIG. 12 is a perspective view from above-left; FIG. 13 is a view from the front with the device's proximal portion lying on cardboard that represents the pubococcygeus muscle, with the distal portion passing downward between the anterior segments of the pubococcygeus muscles; FIG. 14 is a side view of the same arrangement as in FIG. 13; and FIG. 15 shows the device positioned in an anatomic model, again with the proximal portion lying on the anterior segments of the pubococcygeus and the distal portion passing down between the anterior segments. Unlike the previously-described embodiment, the device includes two independent, contiguous arms 60 that do not form a proximal ring. Instead, each contiguous arm includes a proximal portion 62, distal portion 64 that is contiguous with the proximal portion at an inward-turning inflection 66 and terminates at urethral-supporting protrusion 42. As in the FIG. 8-9 embodiment, at the inflection, the device arms both turn inward and angle downward in the same region, which mimics the female anatomy as the vagina passes downward and anteriorly through the space between the anterior segments of the pubococcygeus. The proximal arms may include additional material, such as loops 68. The additional material can provide additional contact surface for muscle support. It can also increase the mass in the proximal portion of the device to help shift the center of gravity to a position above the muscle plane, which can help to stabilize the device in use. The proximal arms may also have distal extensions 70 that provide further support surfaces contacting the pubococcygeus.

The arms may have cross-sections designed to provide differing amounts of flexibility in various directions. For example, it may be desirable to provide a considerable amount of lateral flexibility and elasticity, as discussed below, to facilitate use of a single-size device by women with relatively larger or smaller anatomies. Also, lateral flexibility and elasticity can help promote stabilization of the device against the musculature. At the same time, however, relative rigidity in the vertical direction may be preferred, to help ensure that the device does not migrate and also to ensure that the urethral support protrusion does not deflect from its preferred orientation. The arms may be given cross-sections that are taller than they are wide to achieve greater relative flexibility in the lateral direction compared to the vertical direction. Suitable shapes include I-beam, rectangle, oval, ellipse, etc., any of which would be oriented so that the longer dimension runs vertically.

Figure 16:
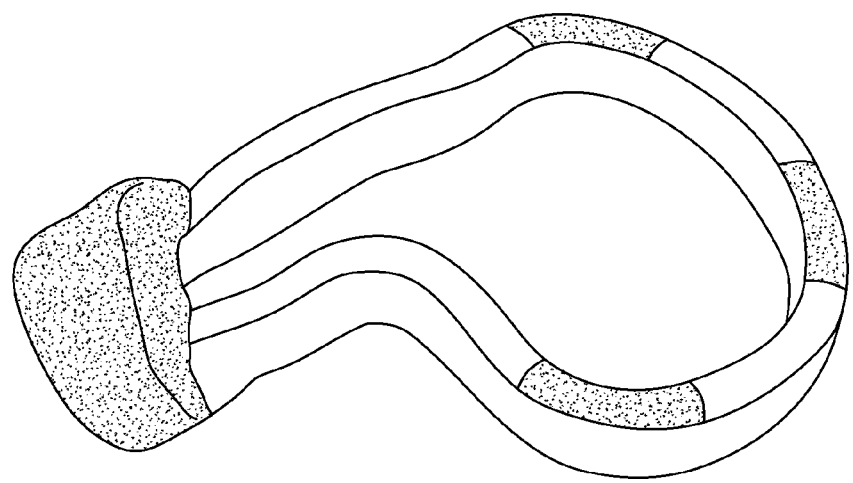
FIG. 16 shows yet another exemplary embodiment.

FIG. 16 shows another embodiment of a device having an inflection that both turns inward and downward.

Figure 17:
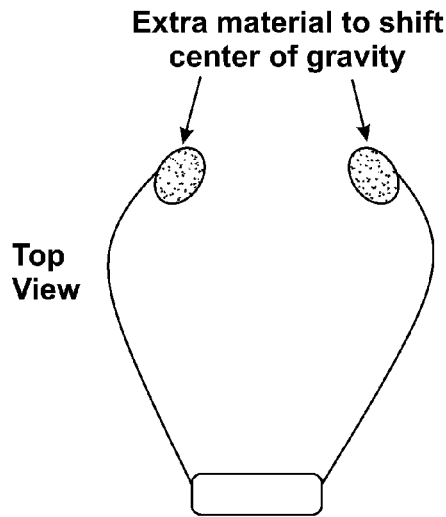
FIGS. 17-19 show additional embodiments of stress urinary incontinence treatment devices.
Figure 18:
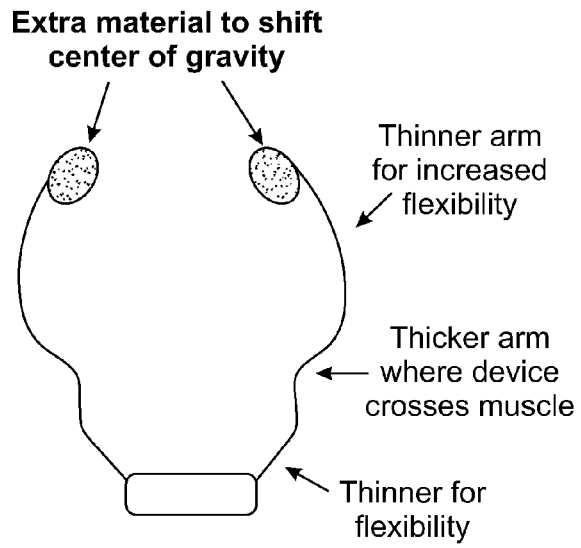
Figure 19:
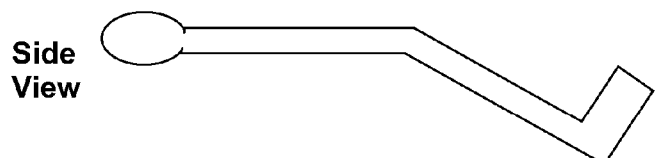

FIGS. 17-19 shows additional embodiments having flexible contiguous arms that diverge as they leave the support protrusion. In a women who needs a larger size device, the arms will open to their full capacity. In a woman requiring a smaller size, the width of the upper arms will be constrained by the pubococcygeus muscles as the lower part of the arms pass between them. This ability to have the pubococcygeus muscles determine the overall width of the device inside the vagina allows a single-sized device to serve a wide variety of women without fitting. FIG. 17 shows a device having arms with a smooth curve, while FIG. 18 shows a device having a "notch" for the pubococcygeus muscles that would help secure the position of the device. FIG. 19 shows a side view of either embodiment.

Figure 20:
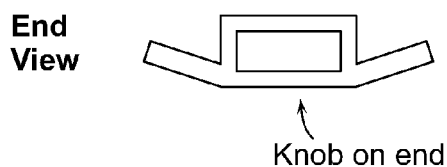
FIGS. 20 and 21 show embodiments of urethral support protrusions.
Figure 21:
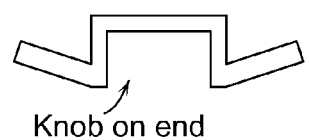

If the arms are made thin and flexible, the center-of-gravity may be shifted downward due to the mass of the support protrusion. Therefore, the protrusion itself may be hollowed out (FIG. 20) and/or have the inferior wall removed (FIG. 21) to shift the center-of-gravity back above the muscle plane. Material may be added to the proximal ends of the proximal arms, as mentioned previously. Although FIGS. 17-18 show the material added medial to the arms, the material may also or instead added lateral to the arms.

Additional features may include:

1. The device is monolithic, meaning that it is formed from a single piece of material without seams. In some embodiments, the device can be formed by multiple parts fixed to one another, made of the same or different materials.

2. The distal portion occupies approx. 40% of the total length.

3. The device can have a "wishbone shape" with a the distal portion curved more steeply (at the disclosed downward angles) with a raised portion or a knob or protrusion at the center point of the wishbone.

4. The proximal portion can have the same or greater rigidity than the distal portion.

5. The device can be fabricated with the same material throughout, or different parts can be made with different materials. The different materials may have different flexibilities. Alternatively, parts made from the same material can have different amounts of flexibility if given different cross-sectional shapes. In some embodiments, the proximal portion may be more flexible than the distal portion.

6. The device can be manufactured with a variety of bioacceptable resins such as poly (methyl methacrylate) and its copolymers, nylon resins (such as Nylon 11 or Nylon 12) and their copolymers, silicone resin, high density and other variants of polyethylene resins and similar polymeric materials. Mixtures of these resins may also be used. The urethral support protrusion may be made of the same material or different materials as the rest of the device. In some embodiments, it may be made of PVA (polyvinyl alcohol) sponge or comparable readily deformable polymer.

7. The device can also be fabricated with a flexible and/or springy metal core with an impermeable resin coating. The metal core may be taller than it is wide (such as a ribbon) to permit more lateral flexibility than vertical flexibility.

8. Radio-opacifying agents can be incorporated into the resins to facilitate radiographic location 9. The device may include a smooth, friction-free surface for ease of insertion, ease of cleansing and reduction of colonization by bacterial species.

A number of exemplary embodiments have been described. Nevertheless, it will be understood that various modifications may be made without departing from the spirit and scope of the disclosure.

We claim:

1. A stress-incontinence treatment device, comprising:
a horizontally-oriented proximal portion; and
a distal portion that:
   is contiguous with the proximal portion at an inflection;
   extends away and downward from the proximal portion at an angle, measured between the proximal and distal portions, in the range of about 100 degrees to about 160 degrees; and
   comprises a protrusion extending transversely to a plane of the distal portion; wherein:
the distal portion is narrower at the inflection than is the proximal portion; and
the device is sized and shaped so that, when positioned in the vagina of a standing woman:
   the proximal portion is supported by the woman's pubococcygeus muscle;
   the distal portion descends between separated anterior fibers of the woman's pubococcygeus muscle; and
   the protrusion is positioned to support the woman's urethra at a mid-urethral position.

2. The device of claim 1, wherein the device is balanced so that it has a center of gravity above the inflection.

3. The device of claim 1, wherein the proximal portion comprises two proximal arms extending proximally from the inflection.

4. The device of claim 3, wherein proximal ends of the arms meet, so that the proximal portion forms a loop.

5. The device of claim 3, wherein the arms terminate in proximal ends that do not meet one another.

6. The device of claim 5, wherein the proximal ends of the arms are thickened to shift the device's center of gravity to a position above the inflection.

7. The device of claim 3, wherein the arms further extend distally in a horizontal plane.

8. The device of claim 3, wherein the distal portion comprises two distal arms extending away and downward from the inflection at the angle, each distal arm contiguous with a respective proximal arm to form a contiguous arm.

9. The device of claim 8, wherein the distal arms terminate with distal ends to which the protrusion is attached.

10. The device of claim 8, wherein the proximal arms are thicker at the inflection than they are proximal to the inflection.

11. The device of claim 8, wherein the proximal arms have cross-sections that are taller than they are wide, so that the proximal arms have greater flexibility laterally than vertically.

12. The device of claim 8, wherein each contiguous arm inflects inward at the inflection.

13. The device of claim 8, wherein the contiguous arms converge toward one another from a widest point at or near the proximal ends of the proximal arms to a narrowest point at or near distal ends of the distal arms.

14. The device of claim 13, wherein the contiguous arms converge smoothly toward one another.

15. The device of claim 13, wherein the contiguous arms converge smoothly proximal to the inflection, converge abruptly at the inflection, and converge smoothly distal to the inflection.

16. The device of claim 3, wherein the proximal arms are biased laterally outward, so that they exhibit a laterally outward reactive force when laterally compressed.

17. The device of claim 1, wherein the angle is in the range of about 115 degrees to about 145 degrees.

18. The device of claim 1, wherein the angle is about 135 degrees.

19. The device of claim 1, wherein the distal portion is more rigid than the proximal portion.

20. The device of claim 1, wherein the device is monolithic.

21. The device of claim 1, wherein the proximal portion is planar.

22. The device of claim 1, wherein the protrusion is positioned at the device's distal-most end.

23. The device of claim 1, wherein the protrusion extends from the distal portion in a direction away from the proximal portion.

24. A method of treating a woman's stress incontinence, comprising:
   inserting the device of claim 1 into the woman's vagina; and
   positioning the device so that when the woman is standing:
      the proximal portion is supported by the woman's pubococcygeus muscle;
      the distal portion descends between separated anterior fibers of the woman's pubococcygeus muscle; and
      the protrusion is positioned to support the woman's urethra at a mid-urethral position.

* * * * *